(12) United States Patent
Kang et al.

(10) Patent No.: US 10,054,595 B2
(45) Date of Patent: Aug. 21, 2018

(54) BLOOD SUGAR MANAGING WATCH AND BLOOD SUGAR MANAGING METHOD

(71) Applicant: ILBS Co., Ltd., Daegu (KR)

(72) Inventors: Soon Ju Kang, Daegu (KR); Kyung Chun Lee, Incheon (KR); Sung Hwa Hong, Daegu (KR)

(73) Assignee: ILBS CO., LTD., Daegu (KR)

( * ) Notice: Subject to any disclaimer, the term of this patent is extended or adjusted under 35 U.S.C. 154(b) by 177 days.

(21) Appl. No.: 15/025,241

(22) PCT Filed: Sep. 19, 2014

(86) PCT No.: PCT/KR2014/008742
§ 371 (c)(1),
(2) Date: Mar. 25, 2016

(87) PCT Pub. No.: WO2015/046823
PCT Pub. Date: Apr. 2, 2015

(65) Prior Publication Data
US 2016/0231325 A1 Aug. 11, 2016

(30) Foreign Application Priority Data
Sep. 27, 2013 (KR) .................. 10-2013-0115555

(51) Int. Cl.
*G01N 27/327* (2006.01)
*G01N 33/66* (2006.01)
(Continued)

(52) U.S. Cl.
CPC .......... *G01N 33/66* (2013.01); *A61B 5/0022* (2013.01); *A61B 5/14532* (2013.01);
(Continued)

(58) Field of Classification Search
CPC ... A61B 5/1486; A61B 5/681; G01N 27/3273
See application file for complete search history.

(56) References Cited

U.S. PATENT DOCUMENTS 7,779,183 B2 * 8/2010 Koehler ................ G16H 40/63
710/72
8,165,893 B1 * 4/2012 Goldberg ............... G06Q 40/08
705/2
(Continued)

FOREIGN PATENT DOCUMENTS

EP 0777123 6/1997
JP H-10504729 5/1998
(Continued)

OTHER PUBLICATIONS

Korean Patent Office computer-generated English langauge tranalation of KR 10-2009-0099147, dated Nov. 20, 2017.*
(Continued)

*Primary Examiner* — Alexander S Noguerola
(74) *Attorney, Agent, or Firm* — Harness, Dickey & Pierce, PLC

(57) ABSTRACT

The present invention relates to a blood sugar managing watch and a blood sugar managing method. The blood sugar managing watch comprises: a housing having a wrist watch shape; a blood sugar strip connector installed on a side of the housing such that a blood sugar strip is to be connected thereto; and a blood sugar meter that is embedded in the housing and automatically activates a blood sugar measurement task to measure the blood sugar of blood on the blood sugar strip when the blood sugar strip is connected to the blood sugar strip connector.

17 Claims, 10 Drawing Sheets

(51) Int. Cl.

| | |
|---|---|
| *A61B 5/157* | (2006.01) |
| *A61B 5/15* | (2006.01) |
| *A61B 5/00* | (2006.01) |
| *A61B 5/145* | (2006.01) |
| *G01N 33/50* | (2006.01) |
| *G01N 27/416* | (2006.01) |
| *G06F 19/00* | (2018.01) |
| *H04M 1/725* | (2006.01) |
| *G16H 40/63* | (2018.01) |

(52) U.S. Cl.
CPC ........ *A61B 5/157* (2013.01); *A61B 5/150022* (2013.01); *A61B 5/150358* (2013.01); *A61B 5/150969* (2013.01); *A61B 5/681* (2013.01); *G01N 27/3272* (2013.01); *G01N 27/3273* (2013.01); *G01N 27/4166* (2013.01); *G01N 33/50* (2013.01); *G06F 19/3418* (2013.01); *G16H 40/63* (2018.01); *H04M 1/7253* (2013.01); *H04M 1/72538* (2013.01); *A61B 2562/0295* (2013.01); *G01N 2400/00* (2013.01)

(56) References Cited

U.S. PATENT DOCUMENTS

| | | | | |
|---|---|---|---|---|
| 8,597,570 | B2 | 12/2013 | Terashima et al. | |
| 9,445,445 | B2 * | 9/2016 | Miller | H04B 5/0031 |
| 2003/0231552 | A1 * | 12/2003 | Markart | G01N 33/528 |
| | | | | 368/10 |
| 2005/0017864 | A1 * | 1/2005 | Tsoukalis | A61B 5/0002 |
| | | | | 340/539.12 |
| 2005/0019848 | A1 | 1/2005 | Lee et al. | |
| 2011/0184267 | A1 * | 7/2011 | Duke | A61B 5/14532 |
| | | | | 600/365 |
| 2011/0257496 | A1 | 10/2011 | Terashima et al. | |
| 2014/0046160 | A1 | 2/2014 | Terashima et al. | |

FOREIGN PATENT DOCUMENTS

| | | | |
|---|---|---|---|
| JP | 2004297353 | A | 10/2004 |
| JP | 2006109895 | A | 4/2006 |
| JP | 2007078403 | | 3/2007 |
| JP | 2008506164 | | 2/2008 |
| KR | 1020020026511 | | 4/2002 |
| KR | 20030088683 | A | 11/2003 |
| KR | 100472092 | B1 | 3/2005 |
| KR | 1020080024220 | | 3/2008 |
| KR | 20090099147 | | 9/2009 |
| KR | 1020100004684 | | 1/2010 |
| KR | 100981137 | B1 | 9/2010 |
| KR | 101000467 | B1 | 12/2010 |
| KR | 20110079894 | | 7/2011 |
| KR | 1020110097628 | | 8/2011 |
| KR | 20130033752 | A | 4/2013 |
| KR | 101278605 | B1 | 6/2013 |
| WO | WO-2005/122608 | | 12/2005 |
| WO | WO-2010052849 | A1 | 5/2010 |
| WO | WO-2011090274 | A2 | 7/2011 |
| WO | WO-2011/129418 | | 10/2011 |

OTHER PUBLICATIONS

Korean Patent Office computer-generated English langauge tranalation of KR 10-1000467, dated Nov. 20, 2017.*
International Search Report PCT/ISA/210 for International Application No. PCT/KR2014/008742 dated Dec. 16, 2014 attached with English translation.
Written Opinion of the International Searching Authority PCT/ISA/237 for International Application No. PCT/KR2014/008742 dated Dec. 16, 2014.
Japanese Office Action dated Feb. 6, 2018 issued in corresponding Japanese Application No. 2016-545678 (with translation).
International Preliminary Report on Patentability dated Mar. 29, 2016 issued in corresponding International Application No. PCT/KR2014/008742 (with English translation).

* cited by examiner

BLOOD SUGAR MANAGING WATCH AND BLOOD SUGAR MANAGING METHOD

CROSS-REFERENCE TO RELATED APPLICATIONS

This application is a national phase under 35 U.S.C. § 371 of PCT International Application No. PCT/KR2014/008742 which has an International filing date of Sep. 19, 2014, which claims priority to Korean Application No. 10-2013-0115555, filed Sep. 27, 2013, the entire contents of each of which are hereby incorporated by reference.

TECHNICAL FIELD

The prevent invention relates to a blood sugar managing watch and a blood sugar managing method.

BACKGROUND ART

As the ubiquitous age arrives thanks to the development of technologies, the people are capable of connecting to a network environment anywhere and anytime. The scale and range of information technologies industries connected with a network are expanded according to the arrival of the ubiquitous age. As an aging society and a silver industry grow, a lot of persons turn attention to health and medical fields. Connection between the ubiquitous technology and a health care enables a lot of persons to be provided with various medical services without going to a hospital. For example, a diabetic patient checks a blood sugar using portable blood sugar measuring equipment without going to a hospital.

However, the burden of chronic disease increases due to the rapid aging of the population, and management of the chronic disease and provision of a preventive service are still insufficient. Since the chronic disease occurs due to wrong habits, it is necessary to prevent and manage the chronic disease in advance and thoroughly. In particular, the diabetes and associated complications are able to be managed and prevented through blood sugar control and education and an exact blood sugar test. Accordingly, it is required a blood sugar managing system capable of minimizing the burden of expense due to the diabetes individually and socially.

A blood sugar patient needs to check a blood sugar periodically. To this end, inconveniently, the diabetic patient puts and holds a blood sugar measurement unit in a separate case or bag to check a blood sugar periodically. Furthermore, conventionally, a user measures a blood sugar using a blood sugar measurement unit and separately records a measured blood sugar value by hand. Alternatively, to record a measured blood sugar value, inconveniently, the user operates another terminal (e.g., a cellular phone, a smart phone, etc.) in measuring a blood sugar and enters the measured blood sugar value into the terminal.

DISCLOSURE OF THE INVENTION

Technical Problem

The prevent invention provides a blood sugar managing watch which is capable of measuring a blood sugar easily and simply and a method for managing a blood sugar.

The prevent invention also provides a blood sugar managing watch and method which transmit blood sugar data, which is measured using the blood sugar managing watch, to a personal mobile terminal or an external device (e.g., an external device of the hospital) using a bidirectional wireless communication so as to conveniently collect measured blood sugar data of a user and make better use of the measured blood sugar data to provide a blood sugar management medical service effectively.

The prevent invention provides a blood sugar managing watch and method which makes it possible to manage a blood sugar thoroughly by notifying a personal terminal of a protector or an external device (e.g., a medical team terminal) of a blood sugar non-measurement notification message when a user does not measure a blood sugar at a predetermined blood sugar management schedule using the blood sugar managing watch.

The problem to be solved by the prevent invention is not limited to the above-mentioned problems. Other problems which are not mentioned will be clearly understood from the following description to those skilled in the art.

Technical Solution

The prevent invention provides a blood sugar managing watch including a housing having a wrist watch shape; a blood sugar strip connector installed on one side of the housing so as to be connected with a blood sugar strip; and a blood sugar meter embedded in the housing, wherein the blood sugar meter measures a blood sugar of blood on the blood sugar strip by automatically activating a blood sugar measurement task when the blood sugar strip is connected to the blood sugar strip connector.

According to an embodiment of the present invention, the blood sugar managing watch further includes a sensing unit installed at the housing and detecting that the blood sugar strip is connected to the blood sugar strip connector to generate an interrupt event; and an interrupt handler installed at the housing and controlling the blood sugar meter in response to the interrupt event so as to activate the blood sugar measurement task.

According to an embodiment of the present invention, the blood sugar managing watch is installed in the housing, and the interrupt handler controls such that the blood sugar measurement task is selectively activated, in response to the interrupt event.

According to an embodiment of the present invention, the blood sugar managing watch further includes a control unit integrating blood sugar measurement data comprising an identifier of the blood sugar managing watch, information of a blood sugar measured by the blood sugar meter, and measurement time information of the blood sugar information in a single data packet and storing the single data packet in the memory.

According to an embodiment of the present invention, the blood sugar managing watch further includes a communication module transmitting the blood sugar measurement data to an external device by the single data packet.

According to an embodiment of the present invention, the blood sugar managing watch further includes a state control unit activating or inactivating a wireless communication function of the communication module in a predetermined period, wherein the control unit broadcasts an advertising message with the wireless communication function activated and sets a wireless network in response to an advertising message input signal from the external device corresponding to the advertising message.

According to an embodiment of the present invention, the communication module transmits a blood sugar non-measurement notification message to the external device when a blood sugar is not measured by the blood sugar meter at a predetermined blood sugar measurement time.

According to an embodiment of the present invention, the blood sugar managing watch further includes a cover opening and closing the blood sugar strip connector.

According to an embodiment of the present invention, the cover is provided in such a way that the blood sugar strip connector is opened and closed according to a manner in which the cover rotates on the basis of a hinge shaft or in such a way that the blood sugar strip connector is opened and closed according to a manner in which the cover slides.

According to an embodiment of the present invention, the blood sugar managing watch further includes an alarm generation unit generating an alarm when a blood sugar value measured by the blood sugar meter is out of a predetermined threshold range.

According to an embodiment of the present invention, the blood sugar managing watch further includes a notification generation unit generating a notification indicating the blood sugar measurement time when a predetermined blood sugar measurement time arrives.

According to an embodiment of the present invention, the blood sugar managing watch further includes a blood sugar measurement schedule management unit transmitting setting information in response to a setting information request message from an external device, receiving new setting information, which is changed by the external device based on the setting information, from the external device, and updating the blood sugar measurement time based on the new setting information.

According to an embodiment of the present invention, the blood sugar strip connector is formed in a direction to face a user's body at a state where the blood sugar managing watch is worn on a user's wrist.

The prevent invention also provides a method for managing a blood sugar using the blood sugar managing watch, the method includes detecting whether a blood sugar strip is connected to a blood sugar strip connector and automatically activating, when the blood sugar strip is connected to the blood sugar strip connector, a blood sugar measurement task of a blood sugar meter to measure a blood sugar of blood on the blood sugar strip.

According to an embodiment of the present invention, the measuring of the blood sugar includes detecting that the blood sugar strip is connected to the blood sugar strip connector to generate an interrupt event; and controlling such that the blood sugar measurement task is selectively activated, in response to the interrupt event.

According to an embodiment of the present invention, the method further includes integrating blood sugar measurement data comprising an identifier of the blood sugar managing watch, information of a blood sugar measured by the blood sugar meter, and measurement time information of the blood sugar information in a single data packet; and transmitting the blood sugar measurement data to an external device by the single data packet.

According to an embodiment of the present invention, the method further includes transmitting setting information in response to a setting information request message from an external device; receiving new setting information, which is changed by the external device based on the setting information, from the external device; updating the blood sugar measurement time based on the new setting information; generating a notification indicating the blood sugar measurement time when a predetermined blood sugar measurement time arrives; and generating an alarm when a blood sugar value measured by the blood sugar meter is out of a predetermined threshold range.

Advantageous Effects

According to an embodiment of the prevent invention, it may be possible to measure a blood sugar in a simple, easy manner, and a user unused to operate an electronic device may measure a blood sugar easily.

Furthermore, according to an embodiment of the prevent invention, blood sugar measurement data may be transmitted to a personal mobile terminal or an external device of the hospital using a bidirectional wireless communication so as to conveniently collect measured blood sugar data of a user, and it may be possible to make better use of the blood sugar measurement data by providing a blood sugar management medical service effectively.

According to embodiments of the prevent invention, also, it may be possible to manage a blood sugar thoroughly by automatically notifying a personal terminal of a protector or an external device (e.g., a medical team terminal) of a blood sugar non-measurement notification message when a user does not measure a blood sugar at a predetermined blood sugar management schedule using the blood sugar managing watch.

The effect of the prevent invention is not limited to the above-mentioned effects. Other effects which are not mentioned will be clearly understood from the following description and accompanying drawings to those skilled in the art.

BEST MODE FOR CARRYING OUT THE INVENTION

Figure 1:
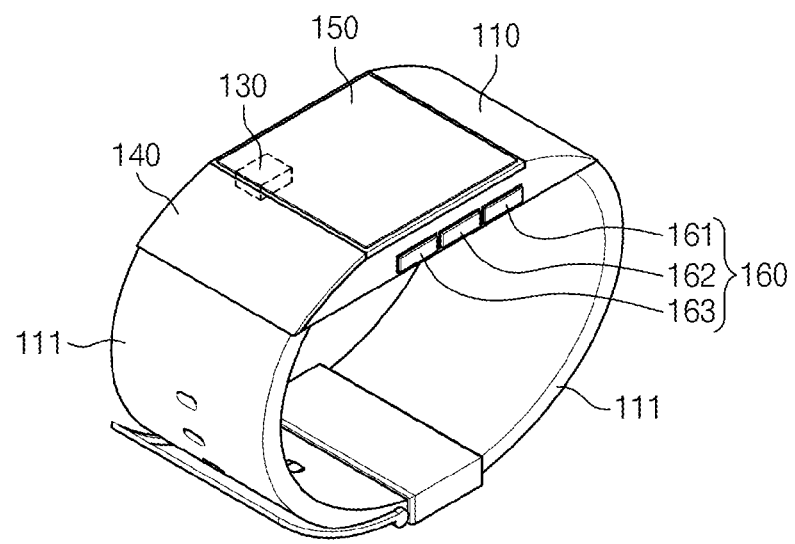
FIG. 1 is a perspective view of a blood sugar managing watch according to an embodiment of the prevent invention.

According to an embodiment of the prevent invention, other advantages and features and methods of accomplishing the same may be understood more readily with reference to the following detailed description of an embodiment and the accompanying drawings. The prevent invention, however, may be embodied in various different forms, and should not be construed as being limited only to the illustrated embodiments. Rather, these embodiments are provided as examples so that this disclosure will be thorough and complete, and will fully convey the concept of the prevent invention to those skilled in the art. The prevent invention may be defined by scope of the claims. Meanwhile, the terminology used herein to describe embodiments of the invention is not intended to limit the scope of the invention.

Even though it is not defined, all terms (including technical or scientific terms) used herein, all terms have the same meaning as being generally accepted by the general technology in the art belonging to prevent invention. It will be further understood that terms used herein should be interpreted as having a meaning that is consistent with their meaning in the context of this disclosure and the relevant art and will not be interpreted in an idealized or overly formal sense unless expressly so defined herein.

It will be understood that when an element is referred to as being "connected" or "coupled" to another element, it can be directly connected or coupled to the other element or intervening elements may be present. General descriptions about the well-known configurations may be omitted so as not to obscure the subject matter of the prevent invention. A configuration which is equal to or corresponds to drawings in the prevent invention is possible using the same reference numerals.

A blood sugar managing watch according to an embodiment of the prevent invention may be a wrist watch-type terminal which include a blood sugar meter therein and is able to measure a blood sugar. The blood sugar managing watch may include a blood sugar strip connector which is installed at a housing provided in a wrist watch shape and is connectable with a blood sugar strip and a blood sugar meter which is embedded in the housing. When the blood sugar meter is connected with the blood sugar strip connector, the blood sugar meter may automatically activate a blood sugar measurement task to measure a blood sugar of blood on a blood sugar strip. In an embodiment, a sensing unit may detect that the blood sugar strip is connected to the blood sugar strip connector and may generate an interrupt event. The interrupt handler may control the blood sugar meter in response to the interrupt event so as to activate the blood sugar measurement task.

According to an embodiment of the prevent invention, the convenience to hold may be secured by embedding the blood sugar meter in the wrist watch-type terminal. A blood sugar may be measured by automatically activating the blood sugar measurement task only through the action that a user connects a blood sugar strip to the blood sugar strip connector included in the housing, thereby making it possible to measure a blood sugar in an easy, simple manner and for a user unused to use an electronic device to measure a blood sugar easily.

The blood sugar managing watch according to an embodiment of the prevent invention may activate a blood sugar measurement task when the blood sugar strip is connected to the blood sugar strip connector and may measure a blood sugar of blood on the blood sugar strip. The blood sugar managing watch may automatically integrate and store an identifier (ID) of the blood sugar managing watch, information of a blood sugar measured by the blood sugar meter, and management time information of the blood sugar information in a single data packet. Since one-to-one correspondence exists between the ID of the blood sugar managing watch, the ID of the blood sugar managing watch may indicate a user ID namely. The blood sugar measurement data integrated in the single data packet may be transmitted to a personal mobile terminal of a user or an external device such as a hospital server using a bidirectional wireless communication.

Accordingly, blood sugar measurement data of a user may be conveniently collected for each user by adding private information of the user to basic medical information (blood sugar information), and the blood sugar measurement data may be overall managed through the external device. Thus, it may be possible to provide an effective blood sugar management medical service by making better use of the blood sugar measurement data. Furthermore, it may be possible to manage a blood sugar thoroughly by notifying a personal terminal of a protector or an external device (e.g., a medical team terminal) of a blood sugar non-measurement notification message when a user does not measure a blood sugar at a predetermined blood sugar management schedule. Also, it may be possible to quickly cope with a dangerous situation that a blood sugar is excessively high.

Figure 2A:
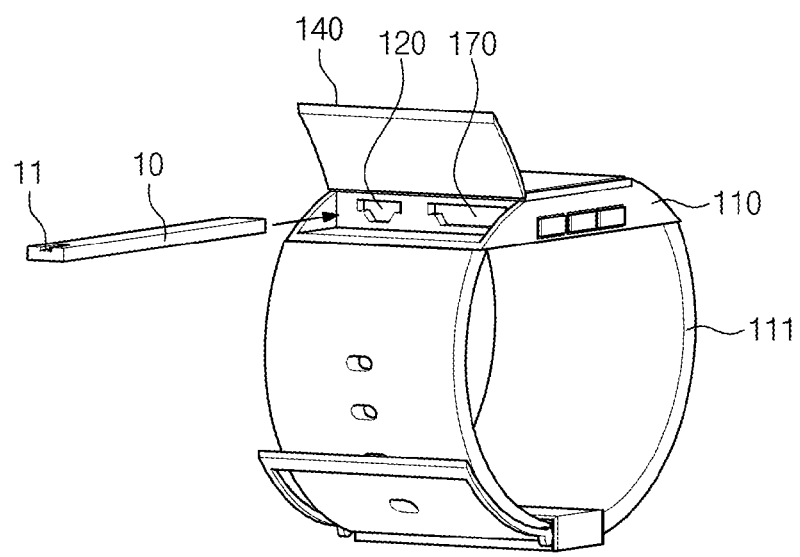
FIG. 2*a* is a perspective view of a cover of a blood sugar managing watch of FIG. 1, shown in an opened state.

FIG. 1 is a perspective view of a blood sugar managing watch according to an embodiment of the prevent invention. FIG. 2A is a perspective view of a cover of a blood sugar managing watch of FIG. 1, shown in an opened state. Referring to. FIGS. 1 and 2A, a blood sugar managing watch 100 according to an embodiment of the prevent invention may be provided in the form of a wrist watch. The blood sugar managing watch 100 may include a housing 110, a blood sugar strip connector 120, a blood sugar meter 130, a cover 140, a display unit 150, a user interface unit 160, and a connector 170.

The housing 110 may have a general wrist watch shape, and opposite ends of the housing 110 may be connected with a wristband-shaped watch strip for wearing on a user's wrist. The blood sugar strip connector 120 may be formed in a shape corresponding to a blood sugar strip 10 so as to be connected with the blood sugar strip 10 and may be installed on one side of the housing 110 so as to be opened or closed by the cover 140. The blood sugar strip connector 120 may be disposed in a direction to face a user's body, with the blood sugar managing watch 100 worn on a user's wrist, thereby improving the convenience of the user in the process to insert the blood sugar strip 10 and gather a blood in measuring a blood sugar.

The blood sugar meter 130 may be embedded in the housing 110. The blood sugar meter 130 may automatically activate a blood sugar measurement task when the blood sugar strip 10 is connected to the blood sugar strip connector 120 and may measure a blood sugar in blood put on the blood sugar strip 10. The cover 140 may be installed in the housing 110 so as to open and close the blood sugar strip connector 120. When the blood sugar strip connector 120 and the connector 170 for connection with a charger, various sensors, or a storage medium are not used, the cover 140 hides the connector 170 and the blood sugar strip connector 120, thereby improving a design function and preventing rainwater or foreign substances from flowing therein. In an embodiment illustrated in FIG. 2A, the cover 140 may be provided to be rotated on the basis of a hinge shaft (not shown) placed at an end side thereof and may be closed or opened by lifting up and down the cover 140. In an embodiment, the cover 140 may be closed or opened when pushed in an on-touch manner, and a spring (not shown) may be installed on a lower surface of the cover 140 such that an opened state is maintained by the spring.

Figure 2B:
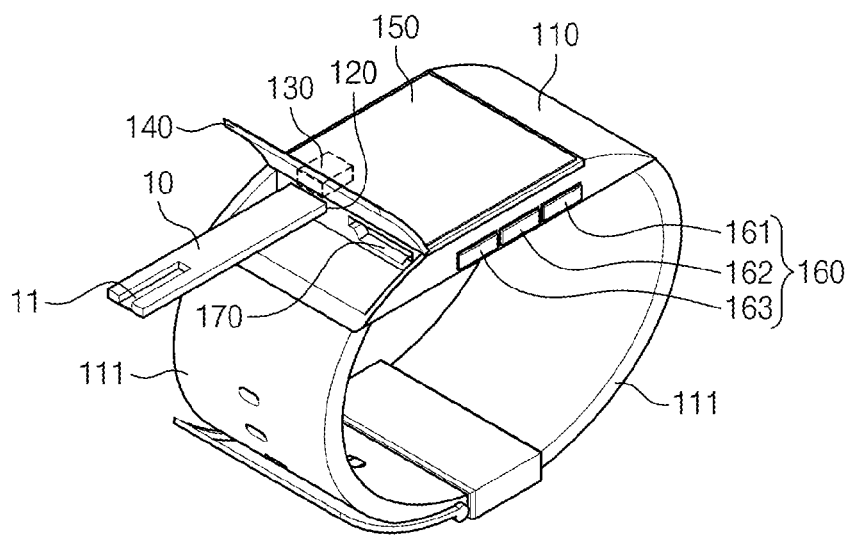
FIG. 2*b* is a perspective view illustrating a state where a blood sugar strip is connected to a blood sugar strip connector of a blood sugar managing watch of FIG. 1.

The blood sugar strip 10 may have a blood insertion portion 11 on which blood gathered for blood sugar measurement is put and may be provided to be inserted into or released from the blood sugar strip connector 120. The blood sugar strip 10, as illustrated in FIG. 2B, may be connected with the blood sugar strip connector 120 such that the blood insertion portion 11 is exposed to the outside, with the cover 140 opened. The display unit 150 may be formed at a front surface of the housing 110 and may display the following on a screen: a date, a time, a measured blood sugar value, a blood sugar schedule notification message, and an abnormal blood sugar alarm message. The display unit 150 may be provided, for example, with a liquid crystal display (LCD) screen.

A user may enter various instructions for performing watch and blood sugar measurement functions through the user interface unit 160. The user interface unit 160 may include, for example, a stopwatch button 161, a menu button 162, and a selection button 163. Like a general wrist watch, the stopwatch button 161 may provide a stopwatch function. The menu button 162 may be provided to confirm data of a blood sugar previously measured or to confirm and set a blood sugar measurement schedule and a notification time. The selection button 163 may be provided to return to a previous menu or end a function after setting a variety of information.

When the blood sugar strip 10 is not connected with the blood sugar strip connector 120, the blood sugar managing watch 100 may display such information as a current date and a current time through the display unit 150 like a basic operation of a general wrist watch. When the blood sugar strip 10 is connected with the blood sugar strip connector 120, the blood sugar managing watch 100 may automatically switch from a general watch mode to a blood sugar measurement mode. In this case, the blood sugar meter 130 may execute a blood sugar measurement task to measure a blood sugar, and the measured blood sugar information may be displayed through the display unit 150.

Even though the user does not operate the user interface unit 160 separately, the user may confirm a blood sugar value by inserting the blood sugar strip 10 into the blood sugar connector 120 and coat the blood sugar strip 10 with the gathered blood. Accordingly, this may make it possible that a user inexperienced to operate an electronic device easily measure a blood sugar. When blood sugar information is measured or when the blood sugar strip 10 is removed from the blood sugar strip connector 120, the blood sugar measurement mode may be again switched to the general watch mode such that general watch functions such as a current date and time display, a stopwatch, and a notification are performed.

Figure 3:
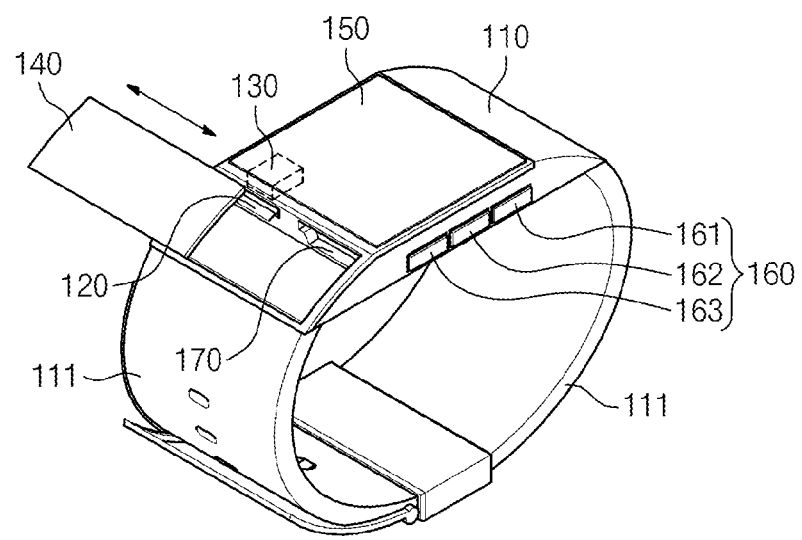
FIG. 3 is a perspective view of a blood sugar managing watch according to another embodiment of the prevent invention.

FIG. 3 is a perspective view of a blood sugar managing watch according to another embodiment of the prevent invention. In describing an embodiment illustrated in FIG. 3, a duplicated description about components the same as or corresponding to an embodiment illustrated in FIGS. 1 and 2B will be omitted. In an embodiment illustrated in FIG. 3, the cover 140 may be provided with a slide open/close structure in which the cover 140 is closed and opened by pushing the cover 140. For example, the cover 140 may have a guide bar (not shown) which slides along a slide groove (not shown) formed at the housing 110. For another example, a slide groove may be formed at the cover 140, and the housing 110 may have a guide bar.

Figure 4:
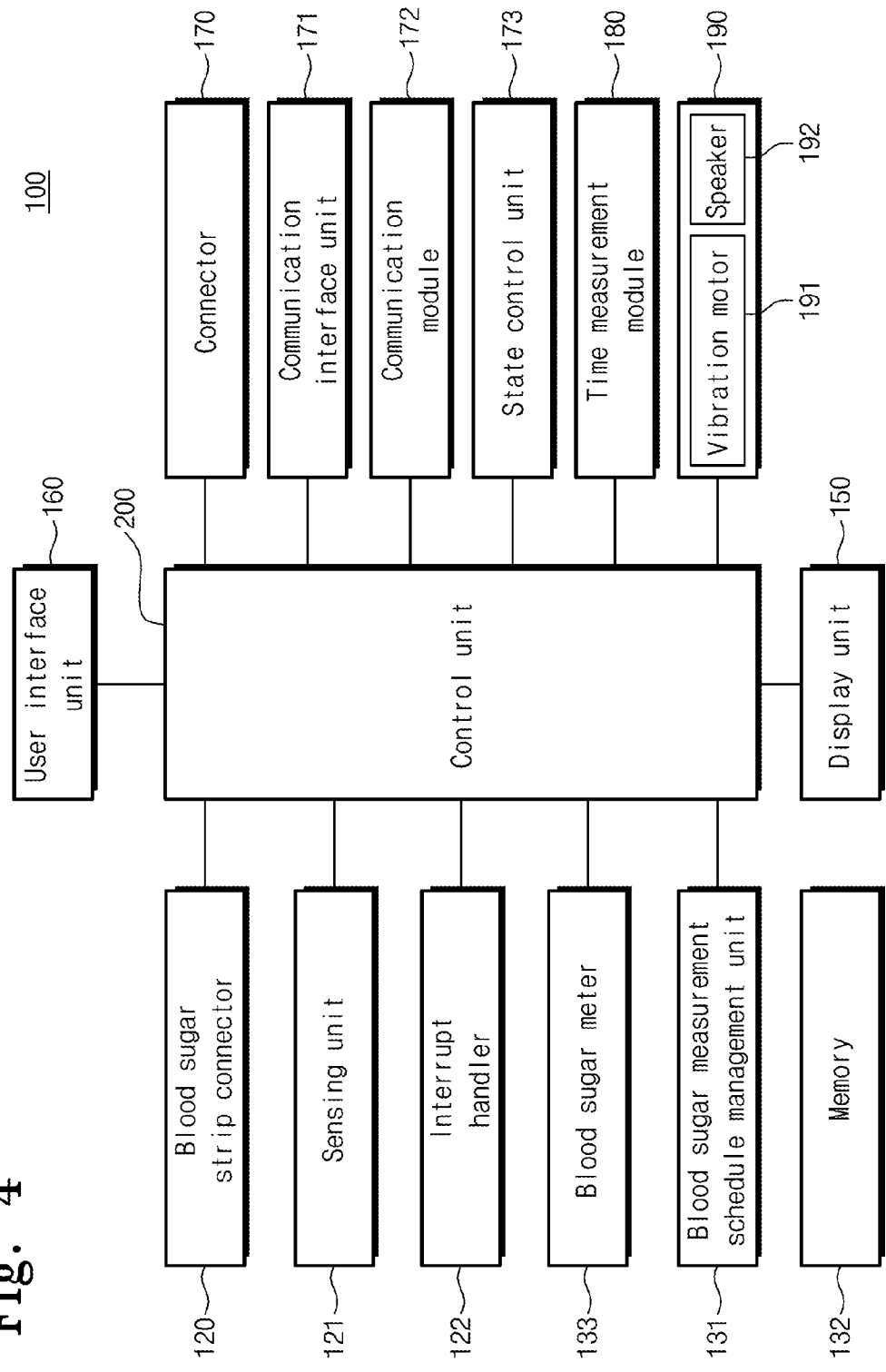
FIG. 4 is a configuration diagram of a blood sugar managing watch according to an embodiment of the prevent invention.
Figure 5:
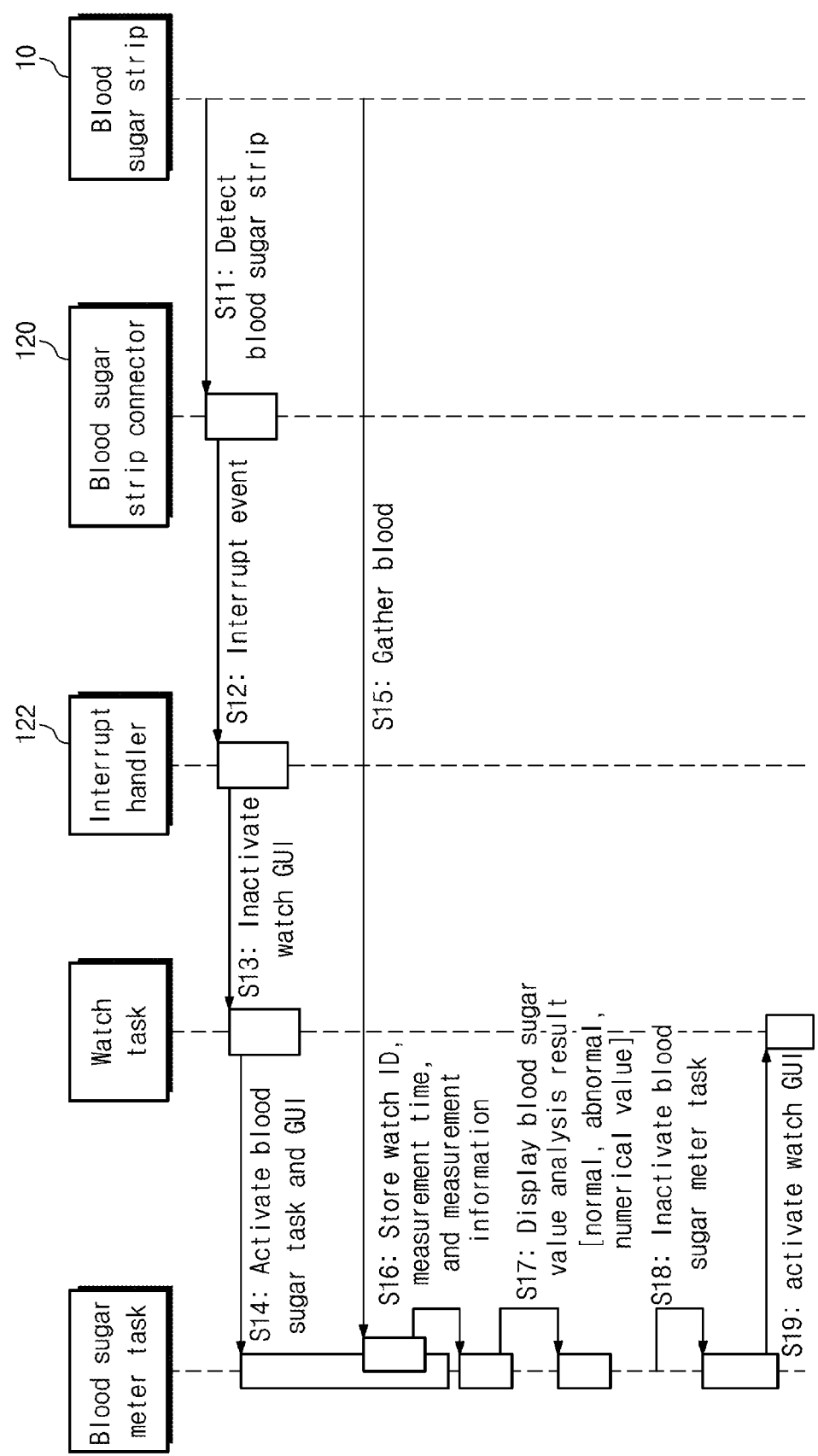
FIG. 5 is a sequence diagram illustrating a blood sugar managing method according to an embodiment of the prevent invention.

FIG. 4 is a configuration diagram of a blood sugar managing watch according to an embodiment of the prevent invention, and FIG. 5 is a sequence diagram illustrating a blood sugar managing method according to an embodiment of the prevent invention. In describing an embodiment illustrated in FIGS. 4 and 5, a duplicated description about components the same as or corresponding to an embodiment illustrated in FIGS. 1 and 3 will be omitted. Referring to FIGS. 1 to 5, the blood sugar managing watch 100 may include the housing 110, the blood sugar strip connector 120, a sensing unit 121, an interrupt handler 122, the blood sugar meter 130, a blood sugar measurement schedule management unit 131, a memory 132, the cover 140, the display unit 150, the user interface unit 160, the connector 170, a communication interface unit 171, a communication module 172, a state control unit 173, a time measurement module 180, a notification generation unit 190, and a control unit 200. A function of each component of the blood sugar managing watch 100 may be controlled by the control unit 200.

The sensing unit 121 may be installed inside the housing 110. The sensing unit 121 may detect that the blood sugar strip 10 is connected to the blood sugar strip connector 120 and may generate an interrupt event as the detection result. For example, when the blood sugar strip 10 is inserted into the blood sugar strip connector 120, the end side of the blood sugar strip 10 may be connected to an electrode (not shown) inside the housing 110, and thus a resistance or power value may be changed. At this time, the sensing unit 121 may recognize a change of a resistance or power value according to coupling of the blood sugar strip 10 and may detect that the blood sugar strip 10 is connected to the blood sugar strip connector 120 (S11). The sensing unit 121 may generate an interrupt event in detecting that the blood sugar strip 10 is connected to the blood sugar strip connector 120 (S12). The sensing unit 121 may be independent of the blood sugar strip connector 120 and may be integrated in the blood sugar strip connector 120.

The interrupt handler 122 may be installed inside the housing 110 and may generate a signal (an activation control signal) for controlling to automatically activate a blood sugar measurement task at the blood sugar meter 130 based on the interrupt event generated from the sensing unit 121. That is, under control of the interrupt handler 122, a task of the blood sugar meter 130 may be selectively activated according to the interrupt event. In an embodiment, the interrupt handler 122 may count an interrupt frequency of the interrupt event; if the interrupt frequency is the same as a set value, the interrupt handler 122 may generate the activation control signal for operating the blood sugar meter 130. If the interrupt frequency is not the same as the set value, a message indicating a device recognition error may be displayed on the display unit 150. The activation control signal generated by the interrupt handler 122 may be inputted to the control unit 200.

The control unit 200 may inactivate a graphical user interface (GUI) of a watch task in response to the activation control signal, may control the blood sugar meter 130 so as to execute a blood sugar measurement task, and may activate the GUI for blood sugar measurement (S14). If blood gathered from a human body is supplied on the blood sugar strip 10 (S15), the blood sugar meter 130 may execute a blood sugar measurement task to measure a blood sugar of the blood on the blood sugar strip 10. For example, a current flowing on the blood sugar strip 10 changes according to the blood sugar, and the blood sugar meter 130 may measure a blood sugar by measuring a current value of the blood sugar strip 10. Blood sugar measured by the blood sugar meter 130 may be stored by the control unit 200 in the memory 132 (S16).

Figure 6:
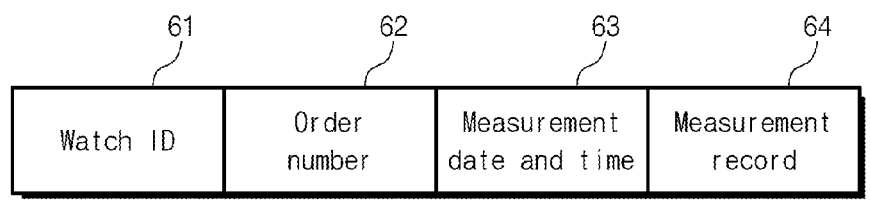
FIG. 6 is a schematic diagram illustrating blood sugar measurement data transmitted from a blood sugar managing watch to an external device, according to an embodiment of the present invention.

In an embodiment, as illustrated in FIG. 6, the control unit 200 may configure blood sugar measurement data 60 by integrating an identifier (ID) 61 of the blood sugar managing watch 100, a serial number 62 indicating a blood sugar measurement order, blood sugar information 64 measured by the blood sugar meter 130, and information 63 of measurement time when the blood sugar information is measured in one data packet and may store the blood sugar measurement data 60 integrated in the single data packet in the memory 132. As such, meaningful data in which private information and blood sugar information of a user is contained may be created by integrating a blood sugar managing watch ID, blood sugar information, and blood sugar measurement time information in one data packet and configuring data. The integrated data may be transmitted to a personal mobile terminal such as a smart phone or an external device such as a server terminal for a medical service, thereby making better use of data.

Referring again to FIGS. 1 to 5, the memory 132 may be, for example, a volatile memory such as a static RAM (SRAM), a dynamic RAM (DRAM), a synchronous DRAM (SDRAM), etc. or a nonvolatile memory such as a read only memory (ROM), a programmable ROM (PROM), an electrically programmable ROM (EPROM), an electrically erasable and programmable ROM (EEPROM), a flash memory device, a phase-change RAM (PRAM), a magnetic RAM (MRAM), a resistive RAM (RRAM), a ferroelectric RAM (FRAM), etc.

The display unit 150 may display a blood sugar value analysis result on a screen. For example, a figure of a measured blood sugar value, a normal or abnormal state, a time when a blood sugar is measured, a time when a blood sugar is to be measured hereafter, etc. may be displayed on the display unit 150 (S17). If the measurement of a blood sugar is completed at the blood sugar meter 130, a task of the blood sugar meter 130 may be inactivated (S18), and a watch GUI may be activated (S19).

The blood sugar measurement schedule management unit 131 may manage a list of schedules when a blood sugar is measured. As an embodiment, the blood sugar measurement schedule management unit 131 may transmit setting information in response to a setting information request message from a personal mobile terminal (a smart phone or etc.) of the user or an external device such as a hospital server or etc., may receive new setting information changed from the setting information from the external device, and may update the blood sugar measurement time based on the new setting information. A function of the blood sugar measurement schedule management unit 131 will be described with reference to FIG. 9.

The connector 170 may be installed on one side of an outer surface of the housing 110 and may be provided to be connected with a charger for charging a battery supplying a power to the blood sugar managing watch 100, various sensors for measuring biosignals such as oxygen saturation, a pulse wave, and a heart rate, and a portable storage medium for storing blood sugar measurement data measured by the blood sugar meter 130 or copying or transferring the blood sugar measurement data stored in the blood sugar managing watch 100.

The communication interface 171 may perform an interface function for transmitting and receiving various messages, signals, data, etc. between the blood sugar managing watch 100 and a device connected to the connector 170. The communication interface 171 may support various devices and may be provided to support different communication protocols. The communication interface 171 may dynamically activate a communication protocol based on a device connected to the connector 170 and may perform communication based on the activated communication protocol.

The communication interface 171 may support, for example, various communication protocols such as UART (Universal Asynchronous Receiver/Transmitter), I²C (Inter-Integrated Circuit bus), SPI (Serial Peripheral Interface), GPIO (General Purpose Input/Output), USB (Universal Serial Bus), PIO (Programmed Input/Output), ADC (Analog-to-Digital Converter), etc.

As an embodiment, when a device is connected to the connector 170, an interrupt event signal may be transferred to the interrupt handler 122 of the blood sugar managing watch 100 from the device connected to the connector 170. The device connected to the connector 170 may generate the interrupt event signal having an interrupt frequency which is previously set for each device. Interrupt event signals with different interrupt frequencies may be transferred to the interrupt handler 122 based on a device connected to the connector 170.

The interrupt handler 122 may count an interrupt frequency of the interrupt event signal. The control unit 200 may automatically recognize a communication protocol, which a device connected to the connector 170 supports, from among communication protocols supported by the communication interface 171 based on the interrupt frequency counted by the interrupt handler 122 and may control the communication interface 171 to activate a corresponding communication protocol. Accordingly, as a communication protocol of the communication interface 171 is dynamically activated according to various devices, it may be possible to set a communication network between a device and the blood sugar managing watch 100 automatically and in real time at the same time when the device is connected to the connector 170.

Figure 7:
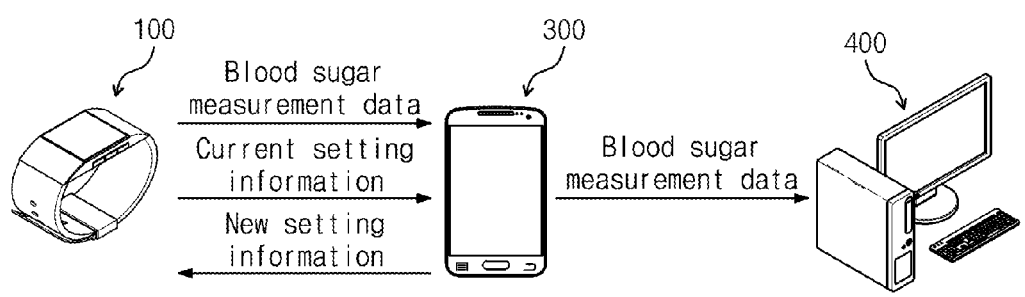
FIG. 7 is a diagram schematically illustrating that blood sugar measurement data is transmitted from a blood sugar managing watch to an external device, according to an embodiment of the present invention.

The communication module 172 may be installed inside the housing 110 and may be a communication interface for transmitting data between a personal mobile terminal of a user or protector and an external device 300 (refer to FIG. 7) such as a hospital server. For example, the communication module 172 may perform functions of transmitting blood sugar measurement data measured by the blood sugar managing watch 100 to the external device 300, receiving blood sugar measurement schedule update data from the external device 300, sending a message indicating blood sugar non-measurement to a personal mobile terminal of a protector and the external device 300 when a user does not measure a blood sugar at a blood sugar measurement schedule, etc. The communication unit 180 may be implemented with a wireless communication device such as Bluetooth, BLE (Bluetooth Low Energy), an LF transceiver, an RF transceiver, or the like and may establish a wireless network between the blood sugar managing watch 100 and the external device 300/400 to transmit and receive data in a real-time streaming manner.

The blood sugar measurement data integrated in a single data packet structure may be transmitted between different external devices 300 and 400. The first external device 300 may be a terminal performing bidirectional communication with the blood sugar managing watch 100, for example, a mobile terminal such as a smart phone or a smart pad of a user or protector. The second external device 400 may be a terminal performing a hospital server function and may receive blood sugar measurement data from a terminal of a user or protector through a mobile web. However, blood sugar measurement data may be directly transmitted from the blood sugar managing watch 110 to the second external device 400 such as a hospital server, or it may be possible to update a blood sugar server and etc. of the blood sugar managing watch 100 by directly transmitting update information from the second external device 400.

Figure 8:
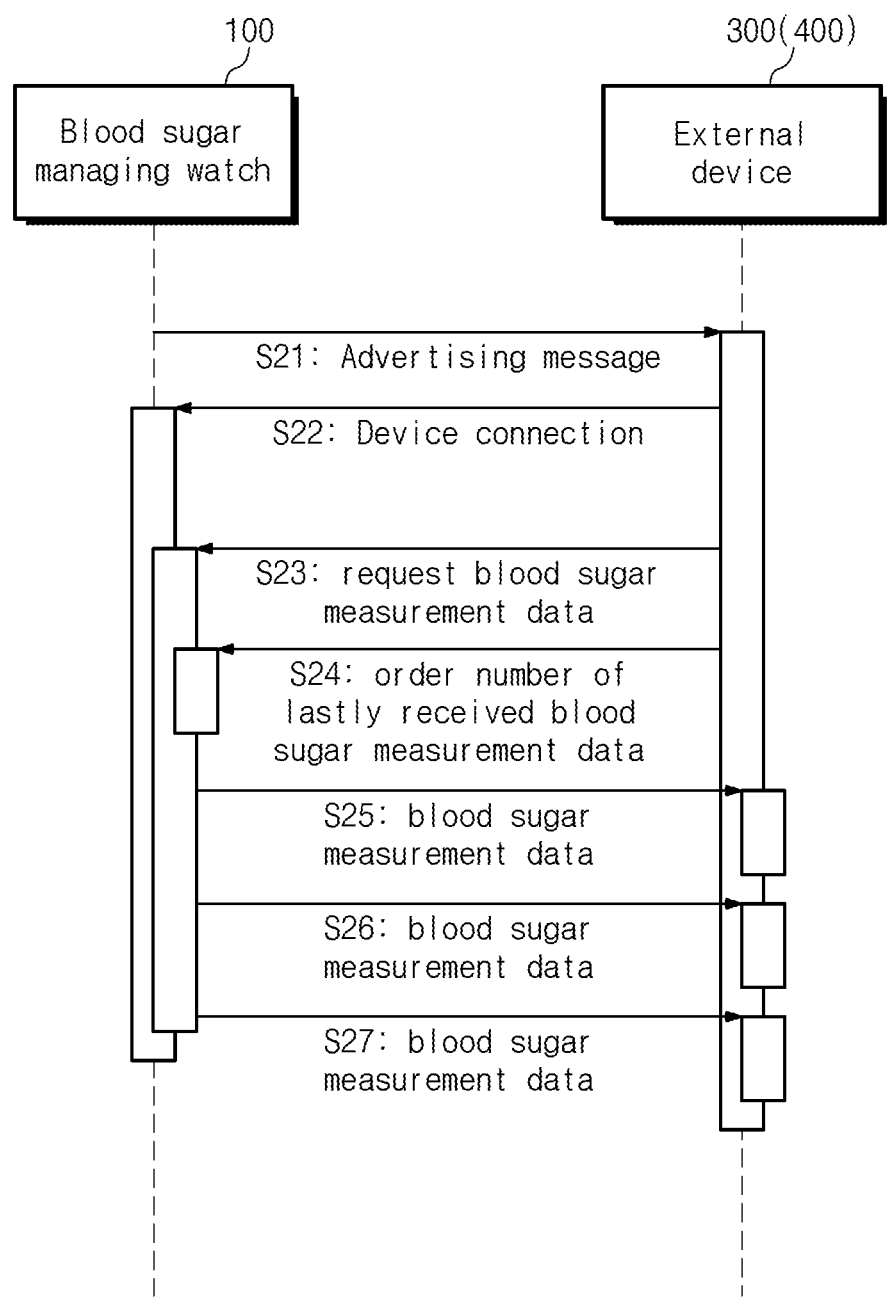
FIG. 8 is a sequence diagram illustrating a manner to transmit data between an external device and a blood sugar managing watch forming a blood sugar managing device according to an embodiment of the prevent invention.

The state control unit 173 may activate or inactivate a wireless communication function of the communication module 172 in a predetermined period so as to minimize power consumption for wireless communication. FIG. 8 is a sequence diagram illustrating a manner to transmit data between an external device and a blood sugar managing watch forming a blood sugar managing device according to an embodiment of the prevent invention. Referring to FIGS. 4 and 8, the control unit 200 of the blood sugar managing watch 100 may broadcast an advertising message, with a wireless communication function activated by the state control unit 173.

For example, when a blood sugar management application is driven by a user, a protector, or a medical team on the external device 300, the external device 300 may detect a surrounding signal to scan an advertising message. The external device 300 may transmit an advertising message input signal to the blood sugar managing watch 100 in response to the advertising message so as to be connected with a device, and in this process, a wireless network may be established between the blood sugar managing watch 100 and the external device 300 (S22). The external device 300 may transmit a blood sugar measurement data request message and order number information of blood sugar measurement data, which is lastly received in a previous communication process, to the blood sugar managing watch 100 (S23, S4). Based on the blood sugar measurement request message, the blood sugar managing watch 100 may transmit blood sugar measurement data, which is cumulated after a lastly transmitted order number, to the external device 300 by the single data packet (S25 to S27).

As an embodiment, in the case where a wireless communication function is inactivated or in the case where wireless communication between the blood sugar managing watch 100 and the external device 300 is not established, for example, an advertising message input signal corresponding to the advertising message is not transmitted from the external device 300 even though a wireless communication function is activated, the control unit 200 of the blood sugar managing watch 100 may store blood sugar measurement data in the memory 132 in a delay tolerant manner; if a wireless network is established between the blood sugar managing watch 100 and the external device 300, the blood sugar managing watch 100 may transmit the stored blood sugar measurement data, that is, blood sugar measurement data, in which the ID of the blood sugar managing watch 100, blood sugar information, and blood sugar measurement time information are integrated, to the external device 300. Accordingly, a user or a protector or medical team of the user may confirm blood sugar measurement data of the user through the external device 300.

A blood sugar measurement value may be processed to one meaningful data by integration with the ID of the blood sugar managing watch and the blood sugar measurement time information, and the processed data may be transmitted to the external device 300 using a wireless communication function so as to be provided to the user or a protector or medical attendant. Accordingly, it may be possible to provide convenience in collecting medical measurement data. In addition, a medical service provider may classify blood sugar measurement data collected from a plurality of users through IDs of blood sugar watches for each user and may confirm blood sugar values about the users in a stream manner on the basis of time. The medical service provider may take measures, for example, may prescribe appropriate drug to a patient or may adjust a blood sugar management schedule.

The time measurement module 180 may be installed inside the housing 110 and may measure time information. In the case where the blood sugar strip 10 is removed from the blood sugar strip connector 120, a watch task corresponding to a function of a general watch may be executed by the control unit 200, and a date and a time which the time measurement module 180 recognizes may be displayed on the display unit 150. If the blood sugar strip 10 is connected to the blood sugar strip connector 120, a watch task may be inactivated, a blood sugar measurement task may initiate, and blood sugar measurement data measured by the blood sugar meter 130 may be displayed on the display unit 150.

If a predetermined blood sugar measurement time arrives, the notification generation unit 190 may generate a notification indicating that the blood sugar measurement time arrives. Accordingly, a user may measure a blood sugar at an accurate time through a function of informing the user of a blood sugar measurement time. The notification generation unit 190 may include, for example, a vibration motor 191 generating a vibration or a speaker 192 generating a notification sound. For another example, the notification generation unit 190 may display a message on the display unit 150 or may notify a user that the blood sugar measurement time arrives, in another manner such as lighting of a notification lamp. Meanwhile, a program dedicated for blood sugar management is running on the external devices 300 and 400 such as a smart phone or a computer of a user, a protector, or a medical team, it may be possible to inform a blood sugar measurement time in manners such as a notification sound and a pop-up event at a corresponding external device 300 or 400.

In an embodiment of the prevent invention, the blood sugar managing watch 100 may further include an alarm generation unit (not shown) which generates alarm when a blood sugar value measured by the blood sugar meter 130 is out of a threshold range. The alarm generation unit may notify a user that a blood sugar value is an abnormal numerical value, using a manner the same as or different from the alarm generation unit 190. For example, in the case where a blood sugar value is out of a threshold range, the alarm generation unit may notify a user of dangerousness in a manner to light a red alarm lamp, in addition to a manner to display a dangerous situation through the display unit 150 or in a manner to generate an alarm sound through a speaker.

In the case where a blood sugar value is out of a normal range, the communication module 172 of the blood sugar managing watch 100 may transmit blood sugar management data and a message, which indicates an abnormal numerical value, to a terminal of a protector or such an external device as a hospital server or may transmit a character message, which indicates a dangerous situation, to a personal mobile terminal of a protector. In the case where a user does not measure a blood sugar at a set blood sugar measurement time, the communication module 172 of the blood sugar managing watch 100 may transmit a message (a blood sugar non-measurement notification message), which indicates that the user does not measure a blood sugar, to a terminal of a protector or such an external device as a hospital server or may transmit a character message (SMS, MMS, etc.), which provides notification that a blood sugar is not measured, to a personal mobile terminal of a protector.

Figure 9:
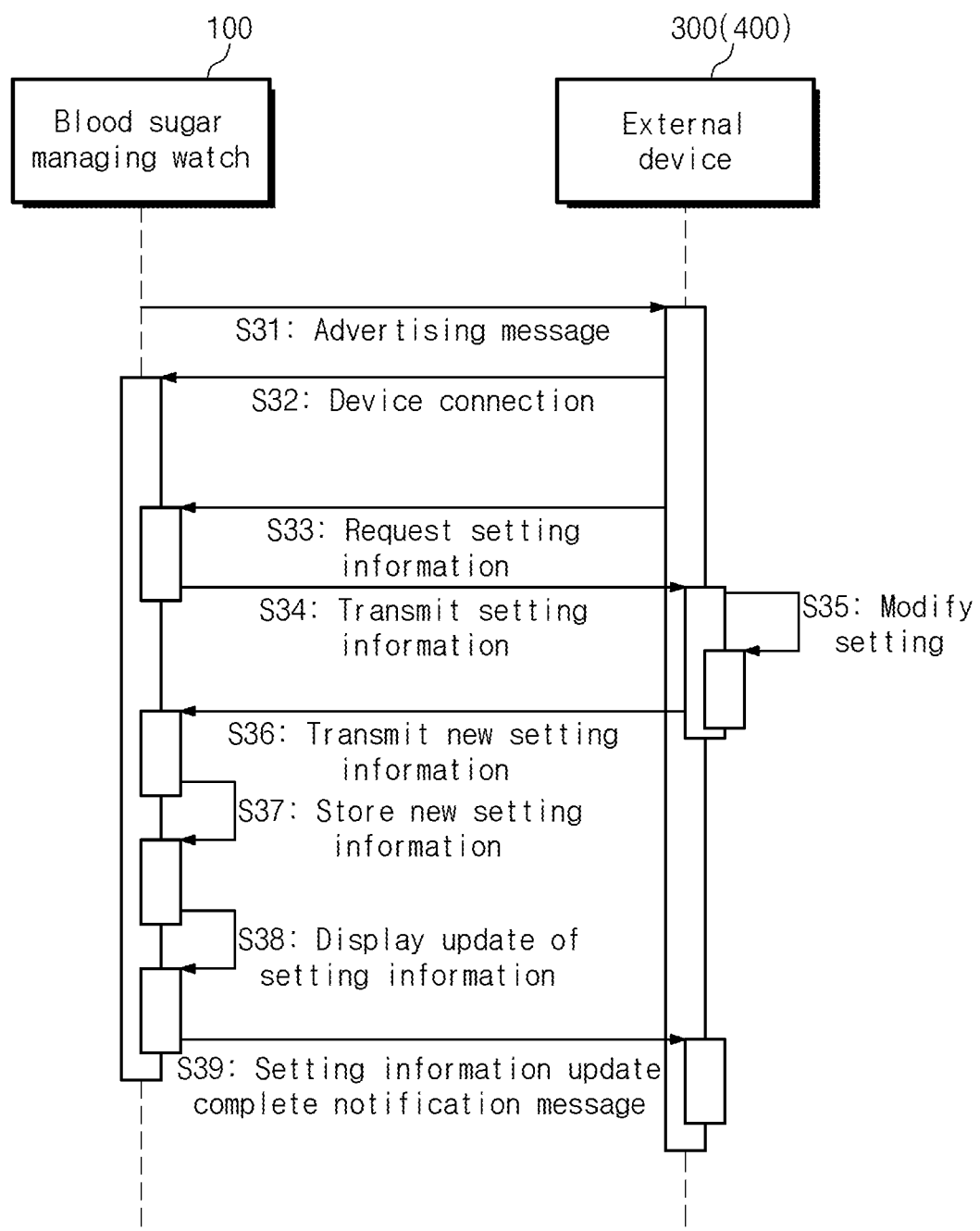
FIG. 9 is a diagram illustrating a sequence for updating a blood sugar measurement schedule by transmitting setting information between a blood sugar managing watch and an external device, according to an embodiment of the prevent invention.

FIG. 9 is a diagram illustrating a sequence for updating a blood sugar measurement schedule by transmitting setting information between a blood sugar managing watch and an external device, according to an embodiment of the prevent invention. Referring to FIGS. 4 and 9, the blood sugar managing watch 100 may broadcast an advertising message (S31), and the external device 300 may transmit an advertising message input signal to the blood sugar managing watch 100 in response to the advertising message so as to be connected with a device (S32). If a setting information request message is transmitted from the external device 300 to the blood sugar managing watch 100 (S33), the blood sugar managing watch 100 may transmit setting information, which is currently set with regard to a blood sugar management schedule, in response to the setting information request message (S34).

Afterward, if a user, a protector, or a medical team changes a blood sugar measurement schedule from previous setting information to new setting information using the external device 300 (S35), the new setting information thus changed may be transmitted to the blood sugar managing watch 100 from the external device 300 (S36). The blood sugar managing watch 100 may update a blood sugar measurement schedule based on the new setting information received from the external device 300 (S37) and may display the updated schedule through the display unit 150 (S38). Finally, the blood sugar managing watch 100 may transmit a notification message, which indicates that the updating of setting information is completed, to the external device 300 (S39). An embodiment of the prevent invention is exemplified in FIG. 9 as a blood sugar management schedule is updated through the external device 300. However, it may be possible to update a blood sugar measurement schedule using the blood sugar managing watch 100.

Figure 10:
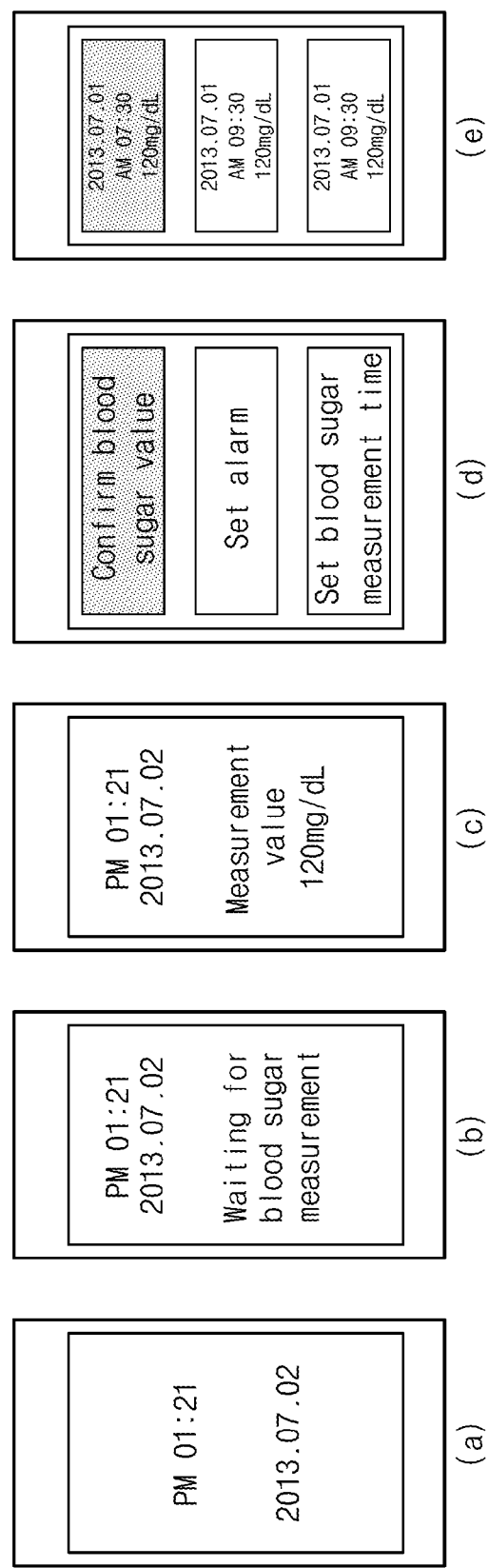
FIG. 10 is a diagram illustrating the procedure for confirming blood sugar measurement data through a display unit of a blood sugar managing watch, according to an embodiment of the prevent invention.

Blood sugar data may be confirmed on the blood sugar managing watch 100 by operating the menu button 162 of the user interface unit 160 or through the external device 300 or 400, for example, through a dedicated program of a smart phone or computer. FIG. 10 is a diagram illustrating the procedure for confirming blood sugar measurement data through a display unit of a blood sugar managing watch, according to an embodiment of the prevent invention. Referring to FIGS. 1 to 3 and 10, in the case where the blood sugar managing watch 100 operates in a watch mode in which a general watch task is performed, as illustrated in (a) of FIG. 10, current date and time may be basically displayed on the display unit 150.

If the blood sugar strip 10 is inserted into the blood sugar strip connector 120, switching from a watch mode to a blood sugar measurement mode may be made. In this case, a blood sugar measurement task may be automatically activated at the blood sugar meter 130, and a message such as "waiting for blood sugar measurement" may be displayed on the display unit 150 as illustrated in (b) of FIG. 10. If the measurement of a blood sugar at the blood sugar meter 130 is completed, a measured value may be displayed on the display unit 150 as illustrated in (c) of FIG. 10, and then the return to the watch mode illustrated in (a) of FIG. 10 may be made.

If a user pushes the menu button 162 in the watch mode, a menu list may be displayed on the display unit 150 as illustrated in (d) of FIG. 10, and a cursor may be placed on a first item of the menu list, that is, such an item as "confirm a blood sugar value". A cursor may move to another adjacent item whenever the menu button 162 is pushed. If the selection button 163 is inputted with a cursor placed on the item "confirm a blood sugar value", a blood sugar value list may be displayed as illustrated in (e) of FIG. 10. The blood sugar value list may include data and time information associated with the measurement of a blood sugar and blood sugar measurement values. A user may confirm a blood sugar value by moving a cursor using the menu button 162, and the return to the menu list screen may be made if inputting the selection button 163.

Figure 11:
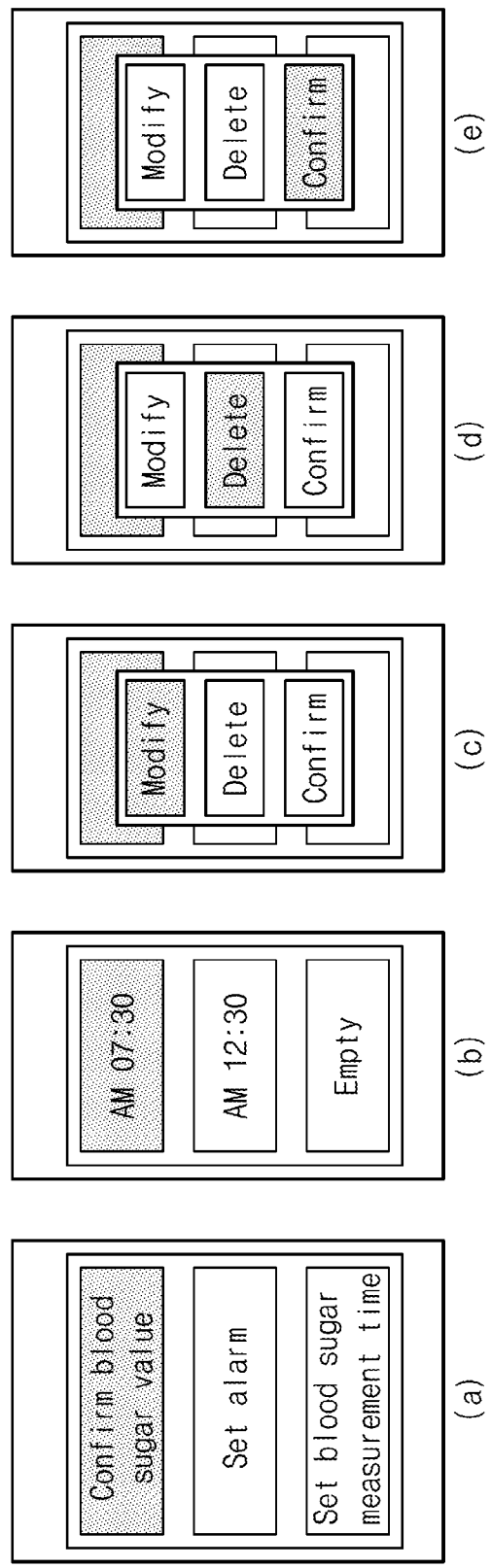
FIG. 11 is a diagram illustrating the procedure for setting a blood sugar measurement time through a blood sugar managing watch, according to an embodiment of the prevent invention.
Figure 12:
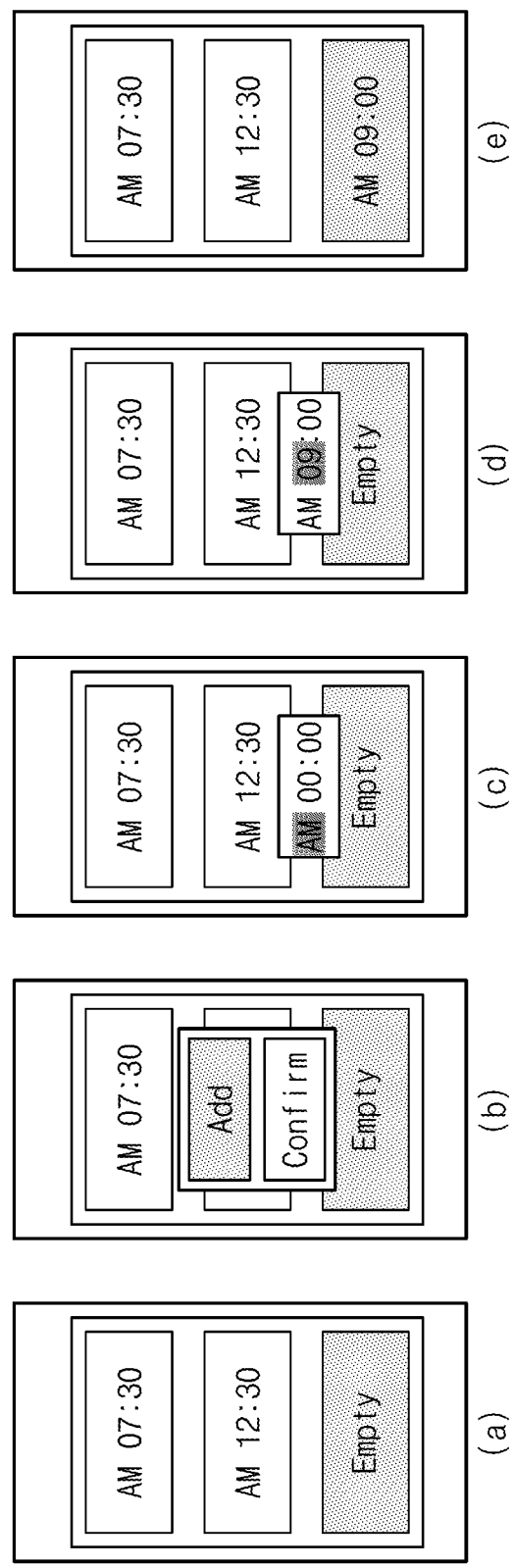
FIG. 12 is a diagram illustrating the procedure for adding a blood sugar measurement schedule through a blood sugar managing watch according to an embodiment of the present invention.

FIG. 11 is a diagram illustrating the procedure for setting a blood sugar measurement time through a blood sugar managing watch, according to an embodiment of the prevent invention. As illustrated in (a) of FIG. 11, if an item "set blood sugar measurement time" displayed on the display unit 150 is selected using the menu button 162 and the selection button 163, a blood sugar measurement schedule list may be displayed as illustrated in (b) of FIG. 11. At this time, after an item which is to be updated is selected from the blood sugar measurement schedule list, as illustrated in (c) to (e) of FIG. 11, a blood sugar measurement schedule may be deleted or modified by selecting a delete or modify item, or the return to the blood sugar measurement schedule list may be made by selecting confirm. Meanwhile, in the case where a new blood sugar measurement schedule is added, an item "Empty" may be selected from a blood sugar measurement schedule list screen illustrated in (a) of FIG. 12; after an item "add" is selected from a screen illustrated in (b) of FIG. 12, information of a time when a blood sugar is to be measured may be inputted as illustrated in (c) to (e) of FIG. 12.

The convenience in measuring a blood sugar may be provided by supporting the blood sugar meter 130, which is embedded in the blood sugar managing watch 100 provided in a wrist watch shape and operates in conjunction therewith, to a patient suffering from a blood sugar disease as a chronic disease or a user interesting in personal health care. According to an embodiment of the prevent invention, all operations for blood sugar measurement and data transmission may be automatically performed only by connecting the blood sugar strip 10 to the blood sugar strip connector 120 and executing an application of the external device 300 or 400, for example, a user smart phone, and an operation for performing a wireless communication function between the blood sugar managing watch 100 and an external device may be minimized. Accordingly, a user may measure a blood sugar easily and simply, and a user, such as an aged patient, unused to operate an electronic device may make it possible to collect blood sugar measurement data without any difficulty.

According to an embodiment of the prevent invention, an alarm may be generated to allow a user to measure a blood sugar on the basis of a set blood sugar measurement schedule, and corresponding information may be automatically notified to a user, a protector, or a medical team using a wireless transmission and reception function of the blood sugar managing watch 100 in the case where a measured blood sugar value corresponds to a dangerous numerical value or in the case where a user does not measure a blood sugar at a blood sugar measurement schedule. Accordingly, it may be possible to manage a blood sugar more thoroughly. This may mean that the diabetes and associated complications are prevented and that social costs due to the blood sugar disease are reduced.

The above embodiment is provided in order to give an understanding of the prevent invention, the scope and spirit of the prevent invention is not be limited thereto, and various modifications possible embodiments therefrom are also understood within the scope of this invention. The technical protection scope of the prevent invention will be defined by the technical spirit of the appended claims, the scope and spirit of the prevent invention is not limited to the wording of the claims, and it is to be understood that the technical value substantially affects the equivalent scope of the invention.

What is claimed is:

1. A blood sugar managing watch, comprising:
   a housing having a wrist-watch shape;
   a blood sugar strip connector installed on one side of the housing so as to be connected with a blood sugar strip;
   a blood sugar meter embedded in the housing, the blood sugar meter being configured to measure a blood sugar of blood on the blood sugar strip by automatically activating a blood sugar measurement task in response to the blood sugar strip being connected to the blood sugar strip connector;
   a device connector being installed on one side of an outer surface of the housing, the device connector configured to be connected with one device of a plurality of devices configured to measure biosignals;
   a communication interface unit installed inside of the housing, the communication interface unit configured to perform an interface function between the blood sugar managing watch and the one device connected to the device connector, the communication interface unit further configured to support different communication protocols for the plurality of devices;
   an interrupt handler installed at the housing; and
   a watch control unit installed inside of the housing,
   wherein the communication interface unit is configured to dynamically activate a communication protocol based on the one device connected to the device connector and perform communication based on the activated communication protocol,
   wherein the plurality of devices are configured to generate interrupt event signals having different interrupt frequencies which are previously set for each device of the plurality of devices,
   wherein one of the interrupt event signals is transferred to the interrupt handler from the one device connected to the device connector in response to the one device being connected to the device connector,
   wherein the interrupt handler is configured to count an interrupt frequency of the one of the interrupt event signals, and
   wherein the watch control unit is configured to automatically recognize the communication protocol, which the one device connected to the device connector supports, from among communication protocols supported by the communication interface unit based on the interrupt frequency counted by the interrupt handler and control the communication interface unit to activate the communication protocol.

2. The blood sugar managing watch of claim 1, further comprising:
   a sensing unit installed at the housing and configured to detect that the blood sugar strip is connected to the blood sugar strip connector and then generate an interrupt event; wherein
   the interrupt handler is configured to control the blood sugar meter in response to the interrupt event so as to activate the blood sugar measurement task.

3. The blood sugar managing watch of claim 2, wherein the interrupt handler is configured to controls the blood sugar meter such that the blood sugar measurement task is selectively activated, in response to the interrupt event.

4. The blood sugar managing watch of claim 1, wherein the watch control unit is configured to integrate blood sugar measurement data comprising an identifier of the blood sugar managing watch, blood sugar information of the blood sugar measured by the blood sugar meter, and measurement time information of the blood sugar information in a single data packet and store the single data packet in a memory.

5. The blood sugar managing watch of claim 4, further comprising:
   a communication module configured to transmit the blood sugar measurement data to an external device by the single data packet.

6. The blood sugar managing watch of claim 5, further comprising:
   a state control unit configured to activate or inactivate a wireless communication function of the communication module in a predetermined period,
   wherein the watch control unit is configured to broadcast an advertising message with the wireless communication function activated and set a wireless network in response to an advertising message input signal from the external device corresponding to the advertising message.

7. The blood sugar managing watch of claim 5, wherein the communication module is configured to transmit a blood sugar non-measurement notification message to the external device in response to blood sugar being not measured by the blood sugar meter at a particular blood sugar measurement time.

8. The blood sugar managing watch of claim 1, further comprising:
   a cover configured to open and close the blood sugar strip connector.

9. The blood sugar managing watch of claim 8, wherein the cover is provided in such a way that the blood sugar strip connector is opened and closed according to a manner in which the cover rotates based on a hinge shaft or in such a way that the blood sugar strip connector is opened and closed according to a manner in which the cover slides.

10. The blood sugar managing watch of claim 1, further comprising:
    an alarm generation unit configured to generate an alarm in response to a blood sugar value measured by the blood sugar meter being out of a particular threshold range.

11. The blood sugar managing watch of claim 1, further comprising:

a notification generation unit configured to generate a notification indicating a blood sugar measurement time in response to a particular blood sugar measurement time arriving.

12. The blood sugar managing watch of claim 11, further comprising:
a blood sugar measurement schedule management unit configured to transmit setting information in response to a setting information request message from an external device, receive new setting information, which is changed by the external device based on the setting information, from the external device, and update the blood sugar measurement time based on the new setting information, the setting information including a blood sugar management schedule.

13. The blood sugar managing watch of claim 1, wherein the blood sugar managing watch is worn on a user's wrist and the blood sugar strip connector is formed in a direction to face a body of the user.

14. A method for managing blood sugar using the blood sugar managing watch of claim 1, the method comprising:
detecting whether a blood sugar strip is connected to a blood sugar strip connector;
automatically activating, in response to the blood sugar strip being connected to the blood sugar strip connector, a blood sugar measurement task of a blood sugar meter to measure a blood sugar of blood on the blood sugar strip;
activating a communication protocol of a communication interface unit of the blood sugar managing watch based on one device of a plurality of devices being connected to a device connector of the blood sugar managing watch, the plurality of devices configured to measure biosignals; and
performing communication based on the activated communication protocol,
wherein the communication interface unit performs an interface function between the blood sugar managing watch and the one device connected to the device connector and supports different communication protocols,
wherein the plurality of devices are configured to generate interrupt event signals having different interrupt frequencies which are previously set for each device of the plurality of devices,
wherein one of the interrupt event signals is transferred to an interrupt handler of the blood sugar managing watch from the one device connected to the device connector based on the one device being connected to the device connector,
wherein the interrupt handler counts an interrupt frequency of the one of the interrupt event signals, and
wherein a watch control unit of the blood sugar managing watch automatically recognizes the communication protocol, which the one device connected to the device connector supports, from among communication protocols supported by the communication interface unit based on the interrupt frequency counted by the interrupt handler and control the communication interface unit to activate the communication protocol based on the one device being connected to the device connector.

15. The method of claim 14, the method further comprising:
generating an interrupt event in response to the blood sugar strip being connected to the blood sugar strip connector;
wherein the blood sugar measurement task is selectively activated, in response to the interrupt event.

16. The method of claim 15, further comprising:
integrating blood sugar measurement data comprising an identifier of the blood sugar managing watch, blood sugar information of the blood sugar measured by the blood sugar meter, and information indicating a blood sugar measurement time of the blood sugar information in a single data packet; and
transmitting the blood sugar measurement data to an external device by the single data packet.

17. The method of claim 14, further comprising:
transmitting setting information in response to a setting information request message from an external device, the setting information including a blood sugar management schedule;
receiving new setting information, which is changed by the external device based on the setting information, from the external device;
updating a blood sugar measurement time based on the new setting information;
generating a notification indicating blood sugar measurement in response to a particular blood sugar measurement time arriving; and
generating an alarm in response to a blood sugar value measured by the blood sugar meter being out of a particular threshold range.

* * * * *